(12) United States Patent
Harding (10) Patent No.: US 9,375,551 B2
(45) Date of Patent: Jun. 28, 2016

(54) NEONATAL AND PEDIATRIC CATHETER SYSTEM

(75) Inventor: Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 316 days.

(21) Appl. No.: 13/223,168

(22) Filed: Aug. 31, 2011

(65) Prior Publication Data

US 2012/0053523 A1  Mar. 1, 2012

Related U.S. Application Data (60) Provisional application No. 61/378,966, filed on Sep. 1, 2010.

(51) Int. Cl.
| | |
|---|---|
| *A61B 17/34* | (2006.01) |
| *A61M 25/06* | (2006.01) |
| *A61M 25/01* | (2006.01) |
| *A61M 25/00* | (2006.01) |
| *A61M 5/32* | (2006.01) |

(52) U.S. Cl.
CPC ........... *A61M 25/0606* (2013.01); *A61M 25/01* (2013.01); *A61M 25/0102* (2013.01); *A61M 25/06* (2013.01); *A61M 25/0612* (2013.01); *A61M 25/0618* (2013.01); *A61M 25/0631* (2013.01); *A61M 5/3243* (2013.01); *A61M 25/0637* (2013.01); *A61M 25/0643* (2013.01); *A61M 25/0662* (2013.01); *A61M 2005/3247* (2013.01); *A61M 2025/0004* (2013.01); *A61M 2025/0006* (2013.01); *A61M 2025/0007* (2013.01); *A61M 2025/0008* (2013.01); *A61M 2025/0681* (2013.01)

(58) Field of Classification Search
CPC ................. A61M 2025/0681; A61M 25/0693; A61M 25/0662; A61M 25/065; A61M 25/0643; A61M 25/0618; A61M 25/0612; A61M 25/06; A61M 2025/0293; A61M 2025/0286; A61M 2025/0228; A61M 2025/0266; A61M 2025/0213; A61M 2025/0206; A61M 25/0102; A61M 25/01; A61M 25/0606; A61M 25/0631; A61M 25/0637
USPC ........................................ 604/164.01–170.03
See application file for complete search history.

(56) References Cited

U.S. PATENT DOCUMENTS

| | | | |
|---|---|---|---|
| 4,445,893 A | 5/1984 | Bodicky | |
| 4,973,313 A * | 11/1990 | Katsaros et al. | 604/165.02 |
| D378,405 S | 3/1997 | Musgrave et al. | |
| 5,676,656 A * | 10/1997 | Brimhall | 604/165.03 |
| 5,772,636 A | 6/1998 | Brimhall et al. | |
| D458,994 S * | 6/2002 | Cindrich | D24/130 |
| 7,722,569 B2 | 5/2010 | Söderholm et al. | |
| 2003/0199827 A1 * | 10/2003 | Thorne | 604/164.08 |
| 2004/0133124 A1 * | 7/2004 | Bates et al. | 600/564 |

(Continued)

FOREIGN PATENT DOCUMENTS

| | | |
|---|---|---|
| EP | 1 568 392 A1 | 8/2005 |
| EP | 2 075 029 A1 | 7/2009 |

(Continued)

*Primary Examiner* — Nathan R Price
*Assistant Examiner* — Anh Bui
(74) *Attorney, Agent, or Firm* — Jeanne Lukasavage; Craig Metcalf; Kirton McConkie (57) ABSTRACT

A neonatal intravascular device having an extension tube to relief stress between a catheter adapter and a luer adapter of the catheter assembly.

14 Claims, 13 Drawing Sheets

(56) References Cited

U.S. PATENT DOCUMENTS

| | | | |
|---|---|---|---|
| 2005/0027263 A1* | 2/2005 | Woehr et al. | 604/263 |
| 2005/0192535 A1* | 9/2005 | Takagi et al. | 604/164.08 |
| 2007/0270758 A1* | 11/2007 | Hanner et al. | 604/177 |
| 2008/0147003 A1* | 6/2008 | Menzi et al. | 604/110 |
| 2008/0243086 A1* | 10/2008 | Hager et al. | 604/198 |
| 2009/0036836 A1 | 2/2009 | Nystrom et al. | |
| 2009/0143808 A1* | 6/2009 | Houser | 606/170 |
| 2009/0318928 A1* | 12/2009 | Purcell et al. | 606/99 |
| 2011/0301551 A1* | 12/2011 | Koehler et al. | 604/263 |

FOREIGN PATENT DOCUMENTS

| | | |
|---|---|---|
| JP | 2005-237638 A | 9/2005 |
| WO | WO 03/066151 A2 | 8/2003 |
| WO | 2005/068006 A1 | 7/2005 |
| WO | WO 2006/082607 A1 | 8/2006 |

* cited by examiner

NEONATAL AND PEDIATRIC CATHETER SYSTEM

RELATED APPLICATIONS

This application claims the benefit of U.S. Provisional Application No. 61/378,966, filed Sep. 1, 2010, entitled NEONATAL AND PEDIATRIC CATHETER SYSTEM, which is incorporated herein by reference.

BACKGROUND OF THE INVENTION

The current invention relates to intravenous devices, specifically to over-the-needle peripheral intravenous (IV) catheters. In particular, the present invention relates to a peripheral IV catheter assembly for use in neonatal and/or pediatric patients.

Catheters are commonly used for a variety of infusion therapies. Catheters are used for infusing fluid, such as normal saline solution, various medicaments, and total parenteral nutrition, into a patient, withdrawing blood from a patient, or monitoring various parameters of the patient's vascular system. A common type of intravenous (IV) catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitate insertion of the catheter into the blood vessel. The catheter and the introducer needle are assembled so that the tip of the introducer needle extends beyond the tip of the catheter with the bevel of the needle facing up away from the patient's skin. The catheter and introducer needle are generally inserted at a shallow angle through the patient's skin into a blood vessel.

The process of placing a catheter in a neonatal or pediatric patient requires the use of a small gauge catheter. Generally, a catheter having a gauge of 24 or 26 is used. Once inserted, it is important to minimize movement of the catheter tube within the patient's small and fragile vein. Excessive movement may result in damage to the patient's vein and/or cause the patient's vein to collapse.

Excessive movement of the catheter tube is commonly caused when a clinician or physician accesses the patient's vasculature by connecting an extension set or syringe to the catheter tube. Further, the bulky interface between the extension set and the catheter tube may create an aggressive transition of the catheter tube into the patient, thereby increasing the likelihood of kinking the catheter tube and/or occluding flow through the catheter tube.

Accordingly, there is a need in the art for a catheter assembly which overcomes challenges inherent in placing and accessing catheters in neonatal patients. Such a catheter assembly and intravenous device is disclosed herein.

BRIEF SUMMARY OF THE INVENTION

In order to overcome the limitations discussed above, the present invention relates to various embodiments of an intravenous device for use in a neonatal patient. Some implementations of the intravenous device include a needle adapter having a proximal end, a distal end, an outer surface and an inner compartment. Partially housed within the inner compartment is a catheter assembly which includes a catheter tube coupled to a catheter adapter, the catheter assembly further including a luer adapter coupled to the catheter adapter via a flexible extension tube. The intravenous device further includes an introducer needle which extends through the inner compartment and the various components of the catheter assembly, wherein a distal tip of the introducer needle is exposed and/or extends beyond a tip of the catheter tube.

In some implementations, the intravenous device further includes a safety clip interposedly positioned between the luer adapter and the proximal end of the needle adapter. The safety clip includes an aperture through which the introducer needle is threaded or inserted. In some aspects of the invention, the safety clip further includes at least one arm having a first surface that is interlockedly coupled with the luer adapter. The at least one arm further includes a second surface that is in contact with a surface of the inner compartment, such that the contact between the second surface of the arm and the surface of the inner compartment maintains the interlocked coupling of the first surface of the arm and the luer adapter.

In some implementations, the inner compartment further includes a recess for receiving the second surface of the arm, wherein upon receiving the second surface of the arm, the first surface of the arm is disengaged from the luer adapter. The safety clip further includes a needle sheath which houses a portion of the introducer needle. Upon removal of the catheter assembly from the inner compartment, the distal tip of the introducer needle is entirely positioned within the needle sheath.

Some aspects of the present invention further provide a method for manufacturing a catheter apparatus, the method including steps for 1) providing a needle adapter having a proximal end, a distal end, an outer surface and an inner compartment; 2) providing a catheter assembly comprising a catheter tube coupled to a catheter adapter, the catheter assembly further including a luer adapter coupled to the catheter adapter via an extension tube, and a fluid pathway extending through the catheter tube, the catheter adapter, the extension tube and the luer adapter; 3) housing a portion of the catheter assembly within the inner compartment of the needle adapter; and 4) providing an introducer needle having a proximal end, a distal end and a body extending therebetween, the proximal end being coupled to the proximal end of the needle adapter and the distal end extending beyond a tip portion of the catheter tube, wherein the body of the introducer needle extends through the fluid pathway of the catheter assembly.

Some implementations of the method of manufacturing further include a step for interposedly positioning a safety clip between a proximal end of the luer adapter and the proximal end of the needle adapter, the safety clip having an aperture through which the introducer needle is inserted, the safety clip further including an arm having a first surface interlockedly coupled to the luer adapter, and a second surface in contact with a surface of the inner compartment, wherein contact between the second surface of the arm and the surface of the inner compartment maintains the interlocked coupling of the first surface of the arm and the luer adapter.

Additional steps of the method include 1) a step for providing a recess on the distal end of the inner compartment for receiving the second surface of the arm; 2) a step for providing the safety clip with a second arm positioned approximately opposite the first arm; 3) a step for providing a groove into a distal end of the inner compartment for receiving a portion of the catheter adapter; 4) a step for coupling a needle sheath to the safety clip; 5) a step for locating a tip portion of the introducer needle within the lumen of the needle sheath when the second surface of the arm is positioned in the recess of the distal end of the inner compartment; and 6) a step for extending a portion of the needle sheath through the fluid pathway of the extension tube, wherein the needle sheath provides a rigid connection between the luer adapter and the catheter adapter for purposes of aiding insertion of the catheter tube during an infusion procedure.

Some implementations of the present invention further include an intravenous device system having a stiffening member having a proximal end, a distal end and a lumen extending therebetween, the proximal end of the stiffening member being fixedly coupled to a proximal surface of the inner compartment of a needle adapter, the distal end extending through a common fluid pathway of a luer adapter and extension tube of a catheter assembly, wherein a portion of an introducer needle is positioned within the lumen of the stiffening member.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1, shown in parts A and B, is an assembled intravenous device in accordance with a representative embodiment of the present invention.

FIG. 2, shown in parts A and B, is a safety clip in accordance with a representative embodiment of the present invention.

FIG. 3, shown in parts A and B, is an intravenous device following insertion of the device during an infusion procedure in accordance with a representative embodiment of the present invention.

FIG. 4, shown in parts A and B, is an intravenous device during removal of the catheter assembly from the needle adapter in accordance with a representative embodiment of the present invention.

FIG. 5, shown in parts A and B, is an intravenous device following removal of the catheter assembly from the needle adapter in accordance with a representative embodiment of the present invention.

FIG. 8, shown in parts A and B, shows a cross-section view of an intravenous device and coupled extension set in accordance with a representative embodiment of the present invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1A:
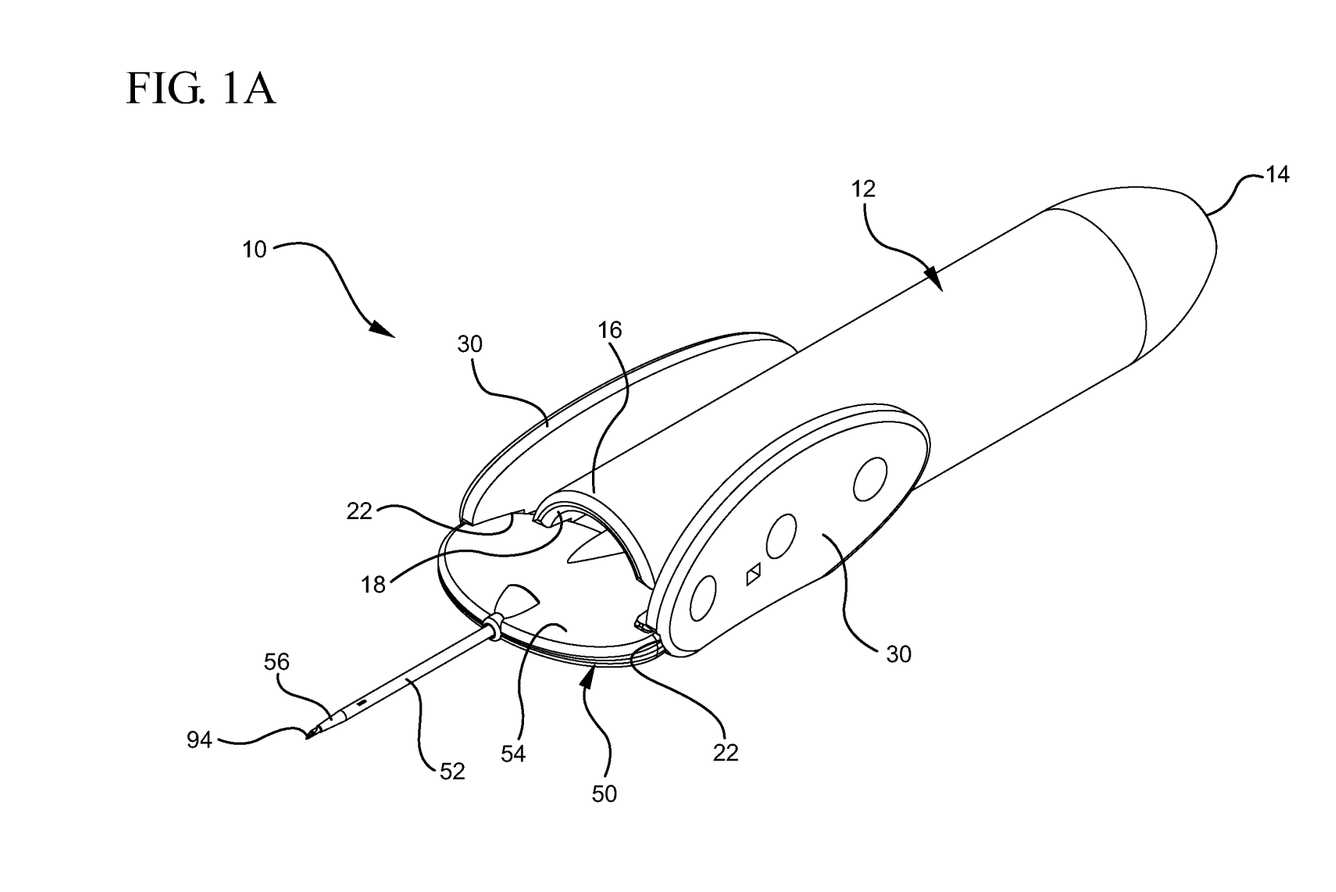
Figure 1B:
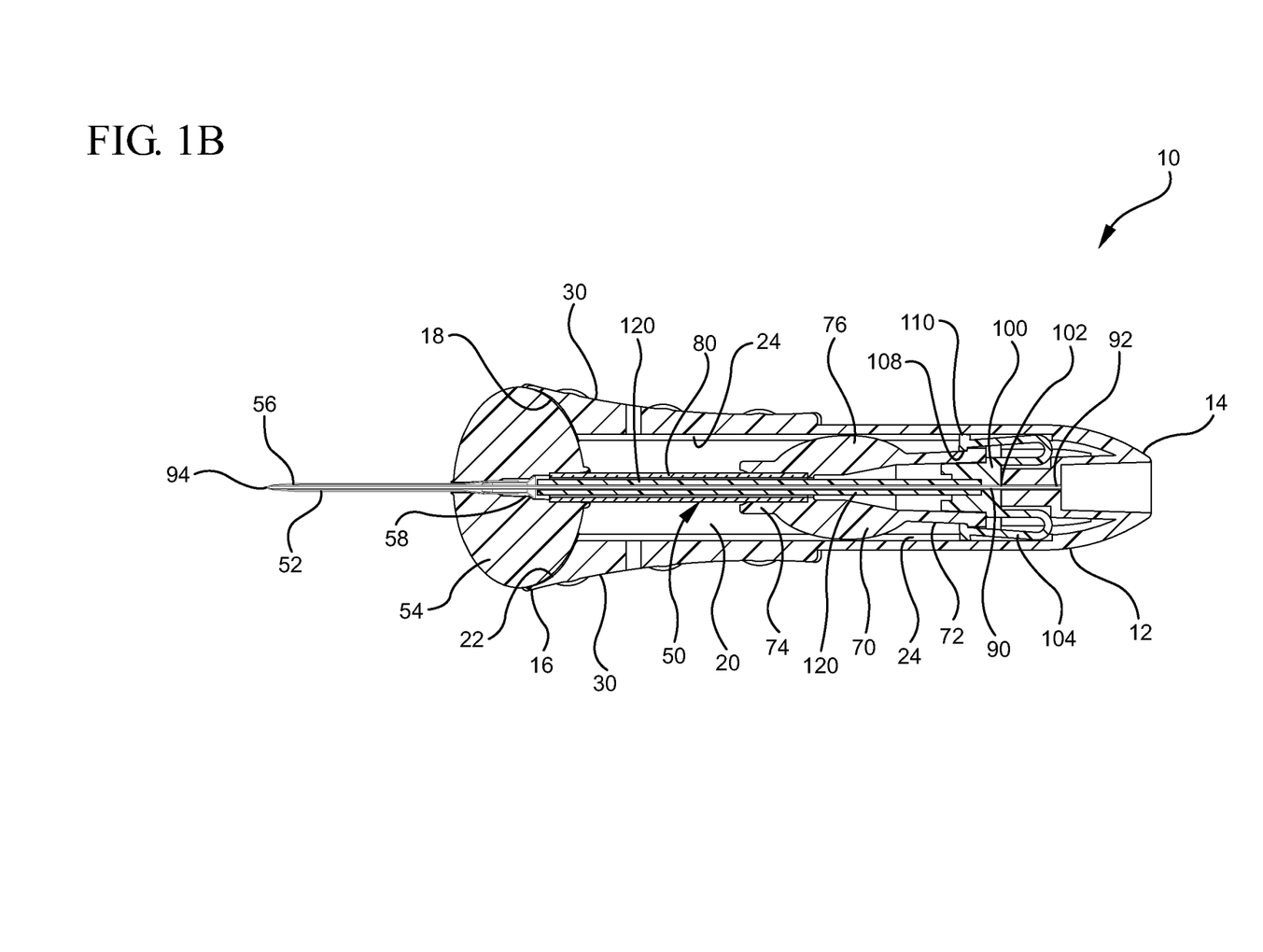

Referring now to FIGS. 1A and 1B, an assembled neonatal intravenous device 10 is shown. Intravenous device 10 generally comprises a needle adapter 12 having a proximal end 14 and a distal 16, wherein the distal end further comprises an opening 18. Needle adapter 12 further comprises an inner compartment 20 sized and configured to house a portion of catheter assembly 50. Inner compartment 20 further comprises various structures and features to enable proper operation of the device 10, as described in detail below.

Catheter assembly 50 generally comprises a catheter tube 52 which is coupled to a catheter adapter 54. Catheter tube 52 may comprise any material or combination of materials known in the art. For example, in some embodiments catheter tube 52 comprises a polymer material. In other embodiments, catheter tube 52 comprises a metallic material.

Catheter tube 52 generally comprises a small gauge catheter, such as a 24 or 26 gauge catheter. The small gauge of catheter tube 52 allows catheterization of infants and other small children whose veins are especially small and fragile. Although the features of the present invention are presented for use in neonatal and pediatric patients, one having skill in the art will appreciate that the features of the present invention may be incorporated into any intravenous device. Once catheterized, the integrity of the patient's vein is maintained by ensuring catheter tube 52 is immobilized within the vein. Thus, in some embodiments catheter adapter 54 is sized and shaped to allow for easy and stable securement of catheter adapter 54 to a small child's arm.

Figure 8A:
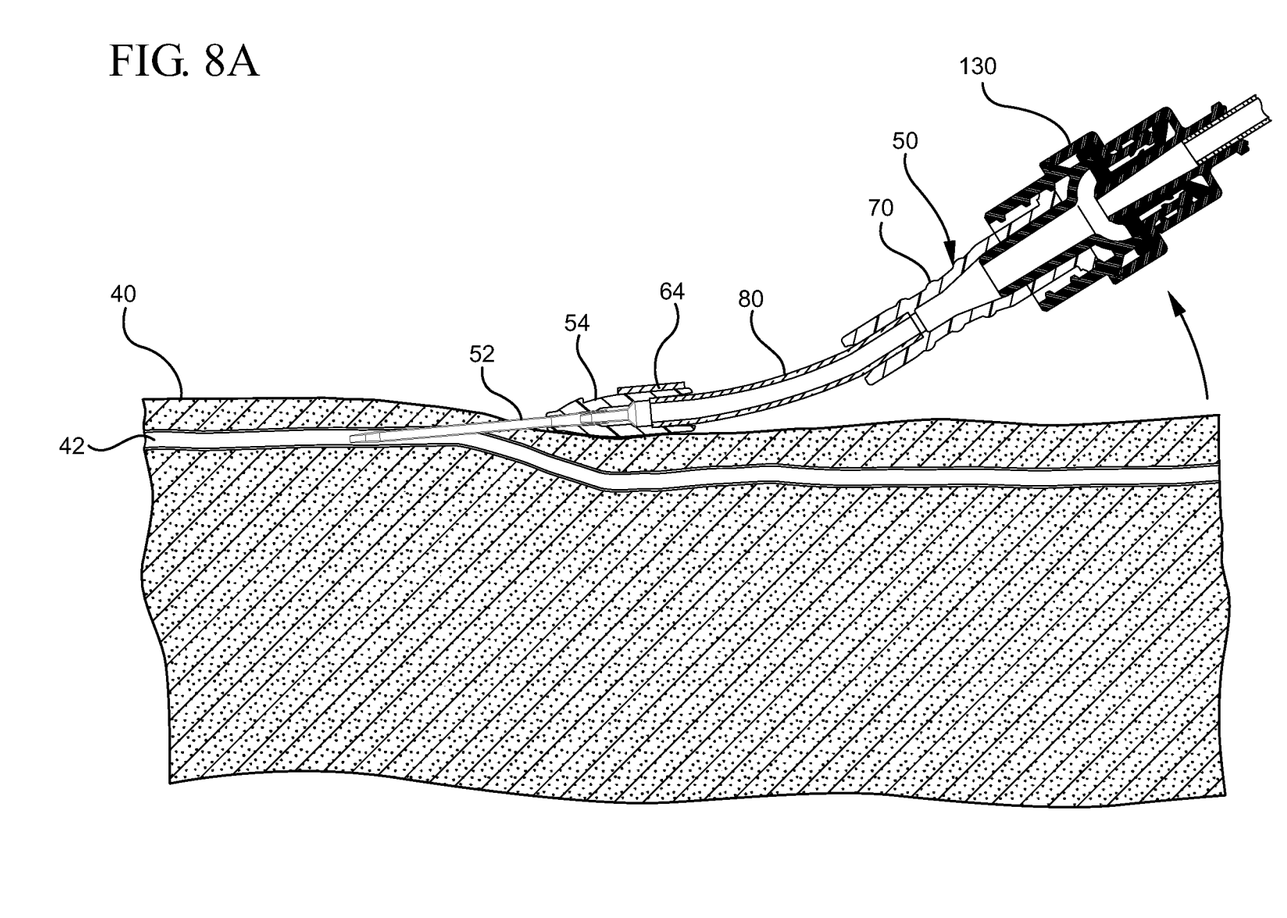
Figure 8B:
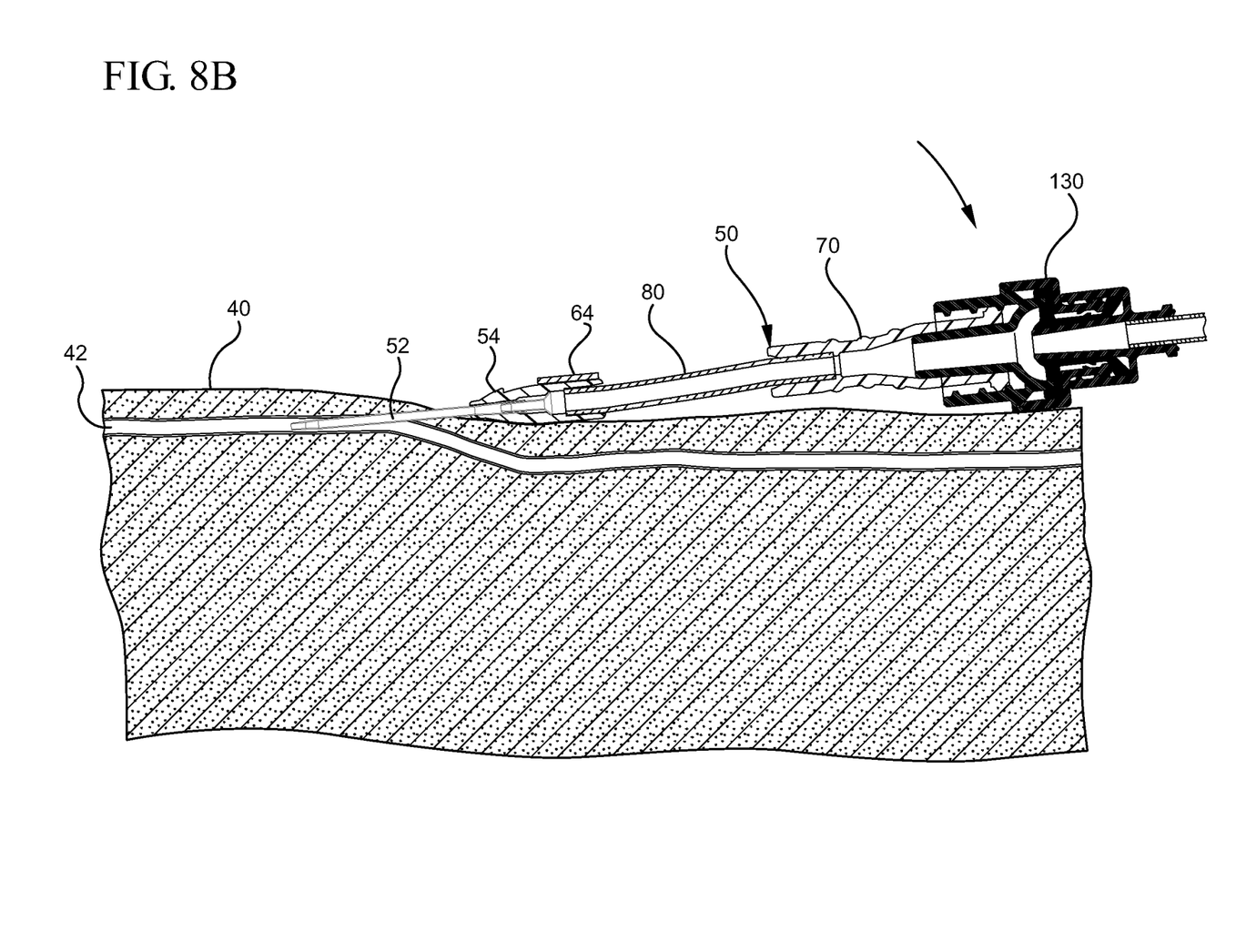

For example, in some embodiments catheter adapter 54 comprises a pliable, disk-shaped material having a width that provides a stable interface with the child's arm or other appendage into which the catheter tube 52 is inserted. Catheter adapter 54 further comprises a low profile thereby minimizing the transition angle of the catheter tube 52 from the catheter adapter 54 to the patient's vein, as shown in FIGS. 8-10B, below.

Catheter assembly 50 further comprises a luer adapter 70 which is coupled to catheter adapter 54 via an extension tube 80. Luer adapter 70 generally comprises a rigid luer connector having a proximal end 72 and a distal end 74. In some embodiments, proximal end 72 comprises a set of threads for compatibly receiving a female luer of an intravenous extension set, such as a length of intravenous tubing, or another compatible device, such as a syringe. In other embodiments, luer adapter 70 comprises features to assist in connecting or disconnecting devices to luer adapter 70. For example, in some embodiments luer adapter 70 comprises a set of wings 76 to increase the surface area or gripping area of luer adapter 70. Luer adapter 70 may further include textural features to increase the friction coefficient of the catheter assembly component.

In some embodiments, extension tube 80 comprises a length of flexible tubing having a proximal end coupled to the distal end 74 of luer adapter 70 and a distal end coupled to the proximal end of catheter adapter 54. Extension tube 80 further comprises an interior space which provides a pathway through which a fluid flows during an infusion procedure. Luer adapter 70, catheter adapter 54 and catheter tube 52 further comprise fluid pathways which are in fluid communication with the interior space of extension tube 80. Thus, catheter tube 52, catheter adapter 54, extension tube 80 and luer adapter 70 form integral catheter assembly 50.

In some embodiments, distal end 74 of luer adapter 70 and the proximal end of catheter adapter 54 further comprise features to prevent occlusion of extension tube 80. For example, in some embodiments the interior surfaces of the openings in which extension tube 80 is inserted into luer adapter 70 and catheter adapter 54 are chamfered. As such, extension tube 80 is provided with an increased range of motion with respect to the interface between extension tube 80 and the relative adapters 54 and 70.

Intravenous device 10 further comprises an introducer needle 90 having a proximal end 92 fixedly coupled to proximal end 14 of needle adapter 12, and a distal tip 94 which extends beyond a tip portion 56 of catheter tube 52. Distal tip 94 generally comprises a beveled cutting edge for providing catheter tube 52 with access to the patient's vein. A body portion of introducer needle 90 extends through the various components of catheter assembly 50, thereby aligning said catheter assembly components 52, 54, 80 and 70.

When fully assembled, various components of catheter assembly 50 are partially or entirely housed within inner compartment 20 of needle adapter 12. For example, in some embodiments luer adapter 70 and extension tube 80 are entirely housed within inner compartment 20, while catheter adapter 54 is only partially housed therein. Needle adapter 12 may include features to facilitate storage of catheter assembly 50 within inner compartment 20. In some embodiments, distal end 16 and opening 18 of needle adapter 12 is modified to include grooves 22 which are configured to received and temporarily retain the proximal, outer edges of catheter adapter 54. The partial housing of catheter adapter 54 within inner compartment 20 positions gripping surfaces 30 of needle housing 12 in close proximity to catheter tube 52 and distal tip 94 of introducer needle 90. As such, a physician is able to grip and maneuver intravascular device 10 with the precision and control necessary to access the patient's small veins. Further, the interface between catheter adapter 54 and groove 22 assists in stabilizing catheter adapter 54 during catheterization.

Figure 2A:
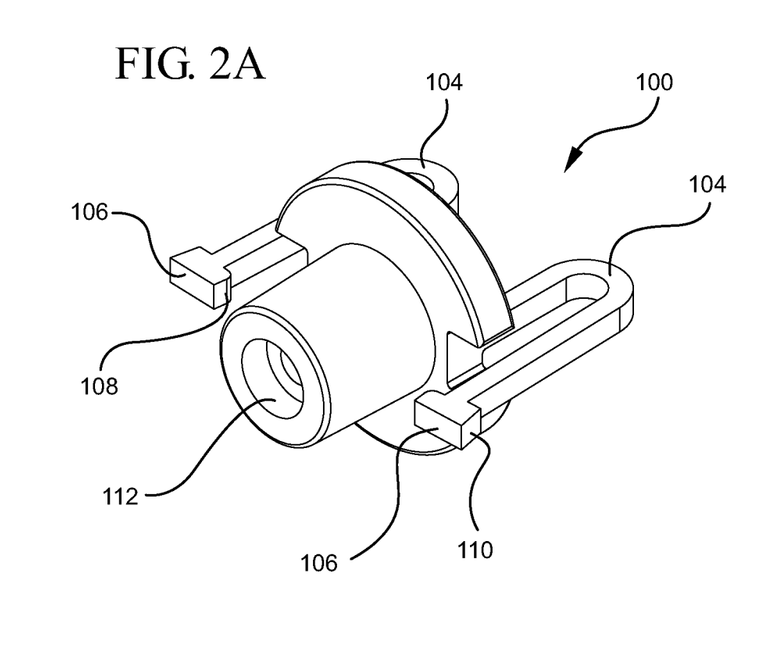
Figure 2B:
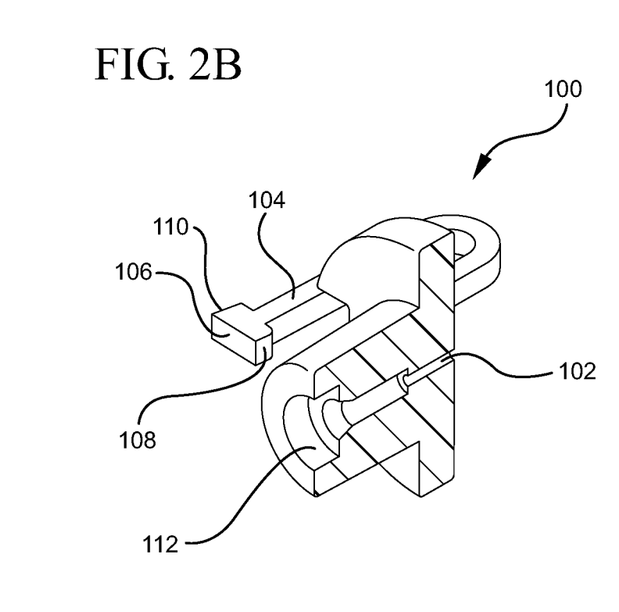

In some embodiments, intravenous device 10 further comprises a safety clip 100. Safety clip 100 is interposedly positioned between a proximal end of luer adapter 70 and the proximal end 14 of needle adapter 12. In some embodiments, safety clip 100 comprises a body having an aperture 102 through which the introducer needle 90 is slidably inserted. Thus, safety clip 100 is permitted to translate within inner compartment 20 in proximal and distal directions over introducer needle 90. A detailed and cross-section view of safety clip 100 is shown in FIGS. 2A and 2B.

With continued reference to FIGS. 1B-2B, in some embodiments safety clip 100 further comprises one or more arms 104. In some embodiments, arms 104 comprise a first end coupled to the body portion of safety clip 100, and a second end 106 which extends outwardly from the body portion. Second end 106 further comprises a first contact surface 108 configured to interlockedly couple to the proximal end 72 of luer adapter 70, and a second contact surface 110 configured to engage and translate within a channel 24 formed on the inner wall surface of inner compartment 20. The interface between second contact surface 110 and channel 24 further inwardly biases arm 104 thereby maintaining the interlocked coupling of first contact surface 108 and luer adapter 70. In some embodiments, first contact surface 108 interlocks with a surface of the luer adapter's set of threads.

In some embodiments, safety clip 100 further comprises a needle sheath 120 having a proximal end coupled to a recess 112 of safety clip 100, and a distal end which extends distally through the fluid pathways of luer adapter 70, extension tube 80 and catheter adapter 54. In some embodiments, needle sheath 120 is a stiffening member. As will be shown later, needle sheath 120 retains or covers distal tip 94 of introducer needle 90 following removal of catheter assembly 50 from needle adapter 12. In some embodiments, needle sheath 120 comprises a rigid structure which reinforces the flexible interconnection between catheter adapter 54 and luer adapter 70 during catheterization. Thus, in some embodiments needle sheath 120 eliminates movement within catheter assembly 50 caused by the flexible extension tube 80.

The methods by which the various components of catheter assembly 50 are assembled may include any techniques or materials known in the art. For example, in some embodiments extension tube 80 is cemented into catheter adapter 54 and luer adapter 70. In other embodiments, extension tube 80 is connected to catheter adapter 54 and luer adapter 70 via a plastic welding technique. Further, in some embodiments extension tube 80 is connected to catheter adapter 54 and luer adapter 70 via a compression fitting. Similarly, catheter tube 52 is secured to catheter adapter 54 via any of the previously discussed methods. Alternatively, catheter tube 52 is coupled to catheter adapter 54 via a swage connector 58.

Figure 3A:
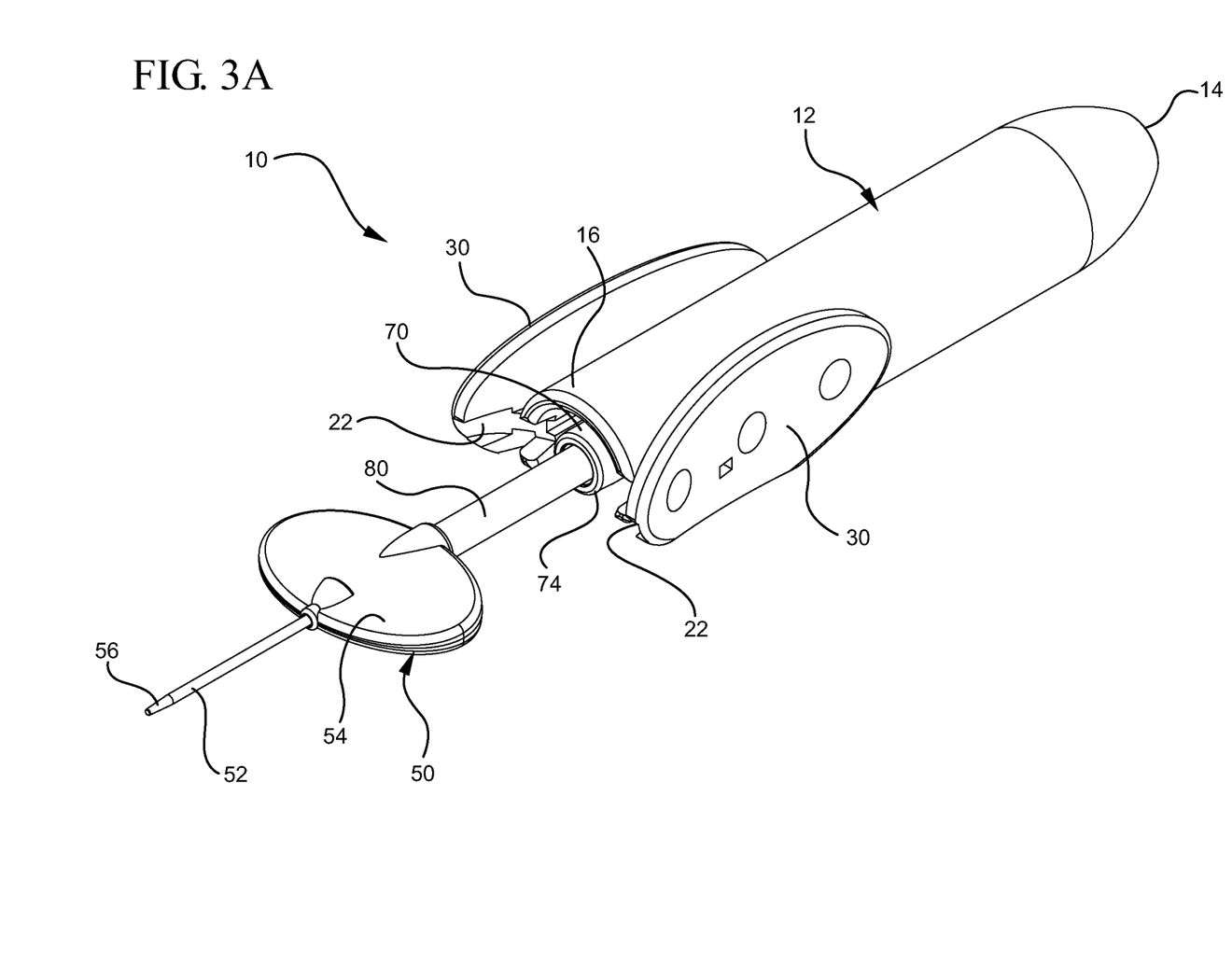
Figure 3B:
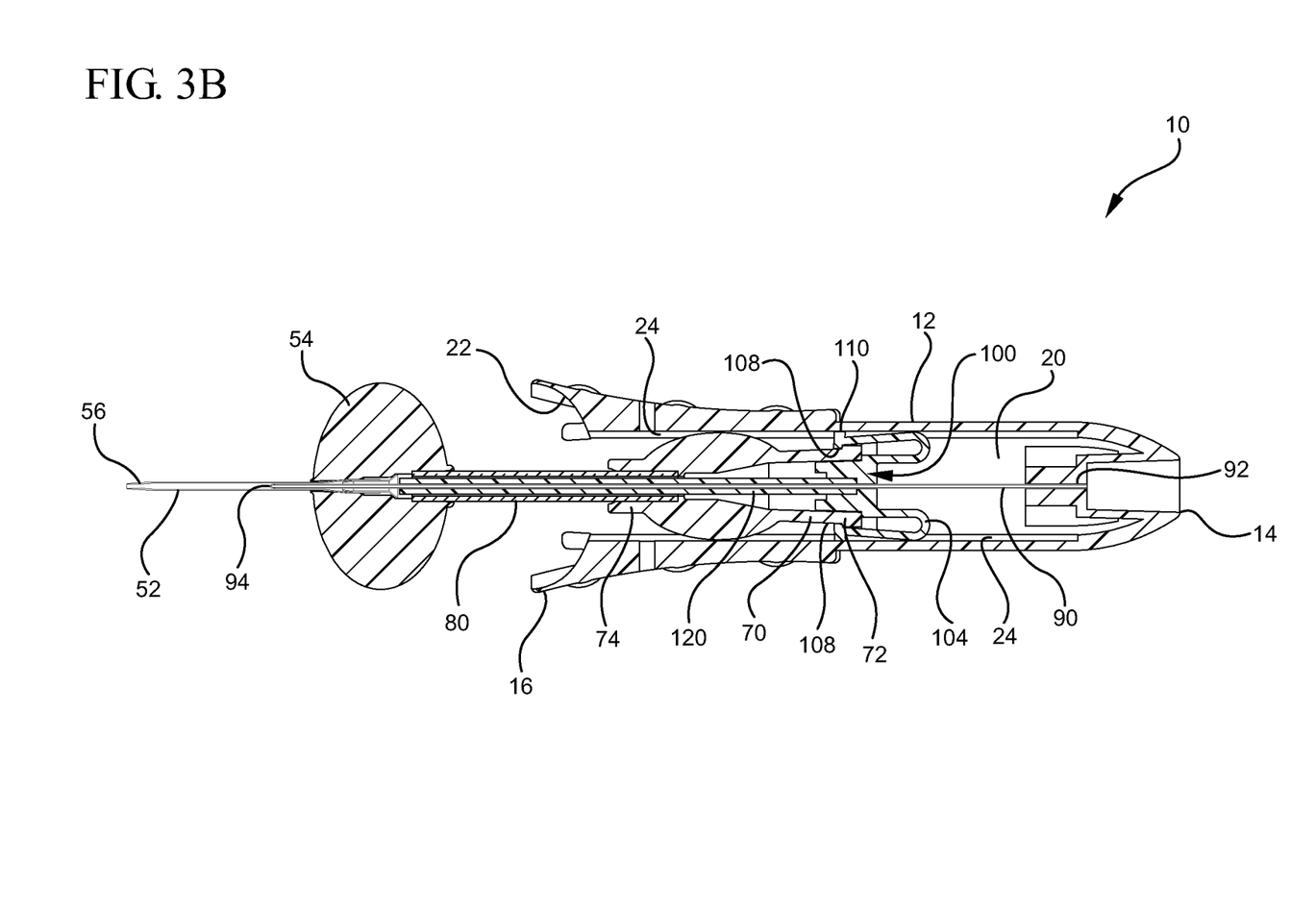

Following insertion of catheter tube 52 into the vasculature of the patient, catheter adapter 54 is immobilized by the physician, such as by holding catheter adapter 54 against the patient's skin. In some embodiment, the pliable nature of catheter adapter 54 aids the physician in immobilizing the position of catheter adapter 54 during removal of introducer needle 90. Introducer needle 90 is withdrawn from catheter tube 52 by moving needle adapter 12 in a proximal direction while catheter adapter 54 is temporarily immobilized, as shown in FIGS. 3A and 3B. Upon moving needle adapter 12 in a proximal direction, catheter adapter 54 is disengaged from grooves 22. Further, the interface between first contact surface 108 and luer adapter 70 causes safety clip 100 to translate through inner compartment 20 in a distal direction with catheter assembly 50. Further, second contact surface 110 is retained and translates within channel 24. The interface between second contact surface 110 and channel 24 further maintains the axial orientation of safety clip 100 while moving through inner compartment 20.

Figure 4A:
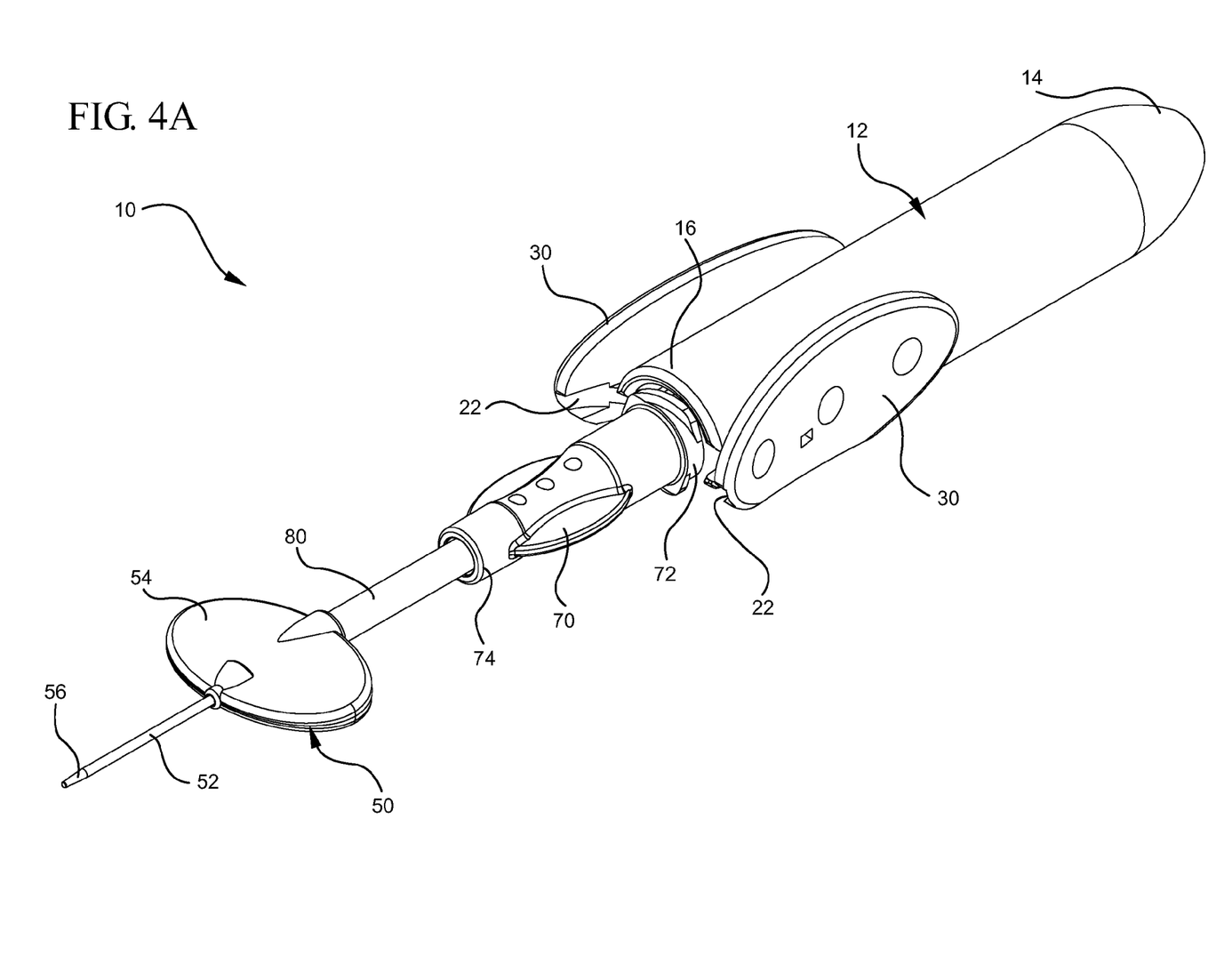
Figure 4B:
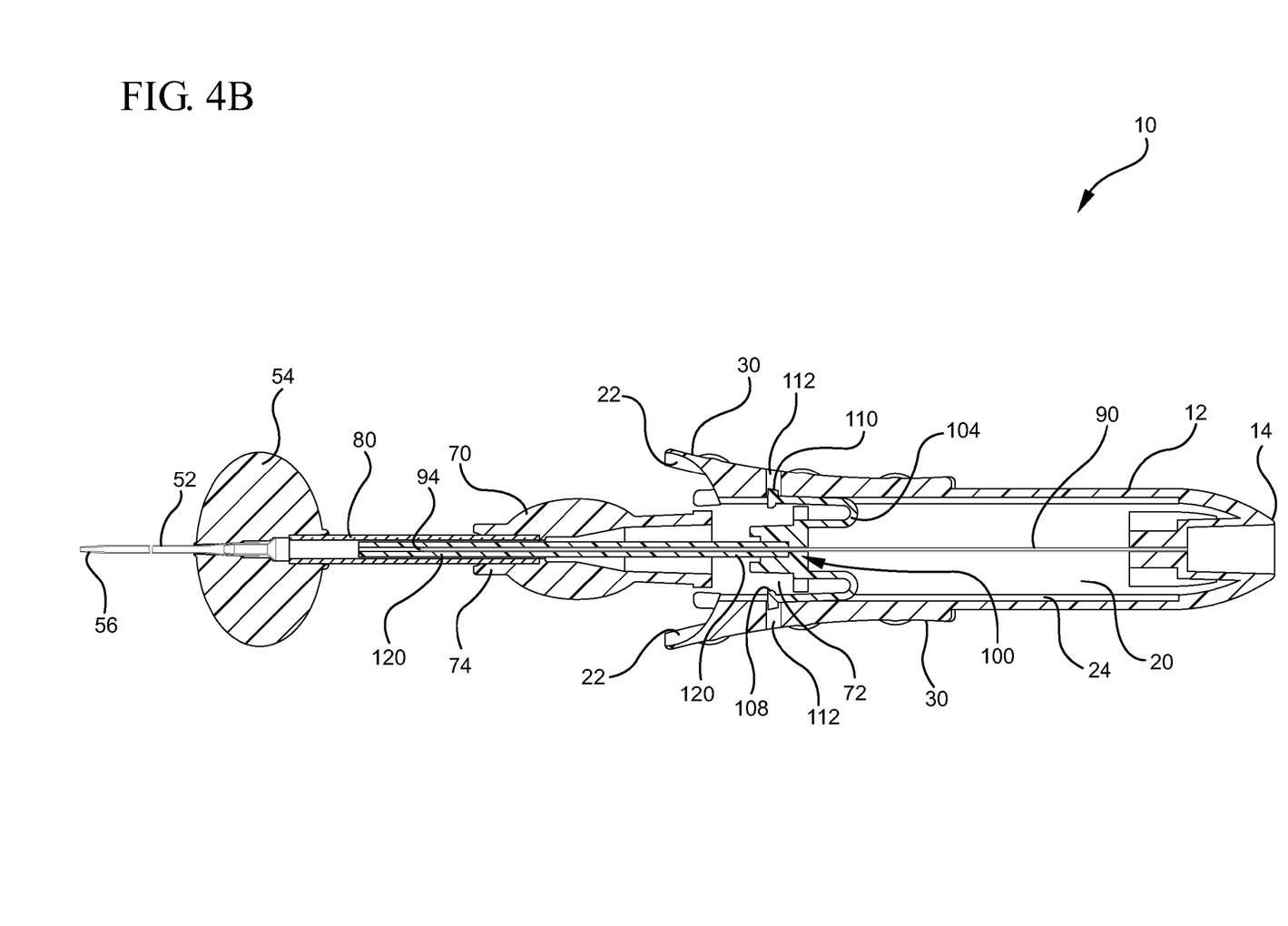

Upon further withdrawal of catheter assembly 50 from inner compartment 20, second contact surface 110 of arms 104 is received by recess 112, as shown in FIGS. 4A and 4B. The interface between second contact surface 110 and recess 112 releases the interlocked connection between first contact surface 108 and luer adapter 70. Thus, luer adapter 70 is disconnected from safety clip 100. Further, the interface between second contact surface 110 and recess 112 arrests the distal translation of safety clip 100 through inner compartment 20. As such, safety clip 100 is retained within the inner compartment 20 of needle adapter 12 while catheter assembly 50 is completely withdrawn from inner compartment 20, as shown in FIGS. 5A and 5B.

In some embodiments, the position of recess 112 along the inner wall surface of inner compartment 20 is configured such that distal tip 94 of introducer needle 90 is entirely positioned or contained within needle sheath 120 at the point in which second contact surface 110 is retained within recess 112. Thus, upon complete removal of catheter assembly 50 from needle adapter 12, distal needle tip 94 is safely shielded within needle sheath 120 thereby preventing a needlestick injury or undesirable exposure to blood or other fluids which remain on the introducer needle.

Figure 5A:
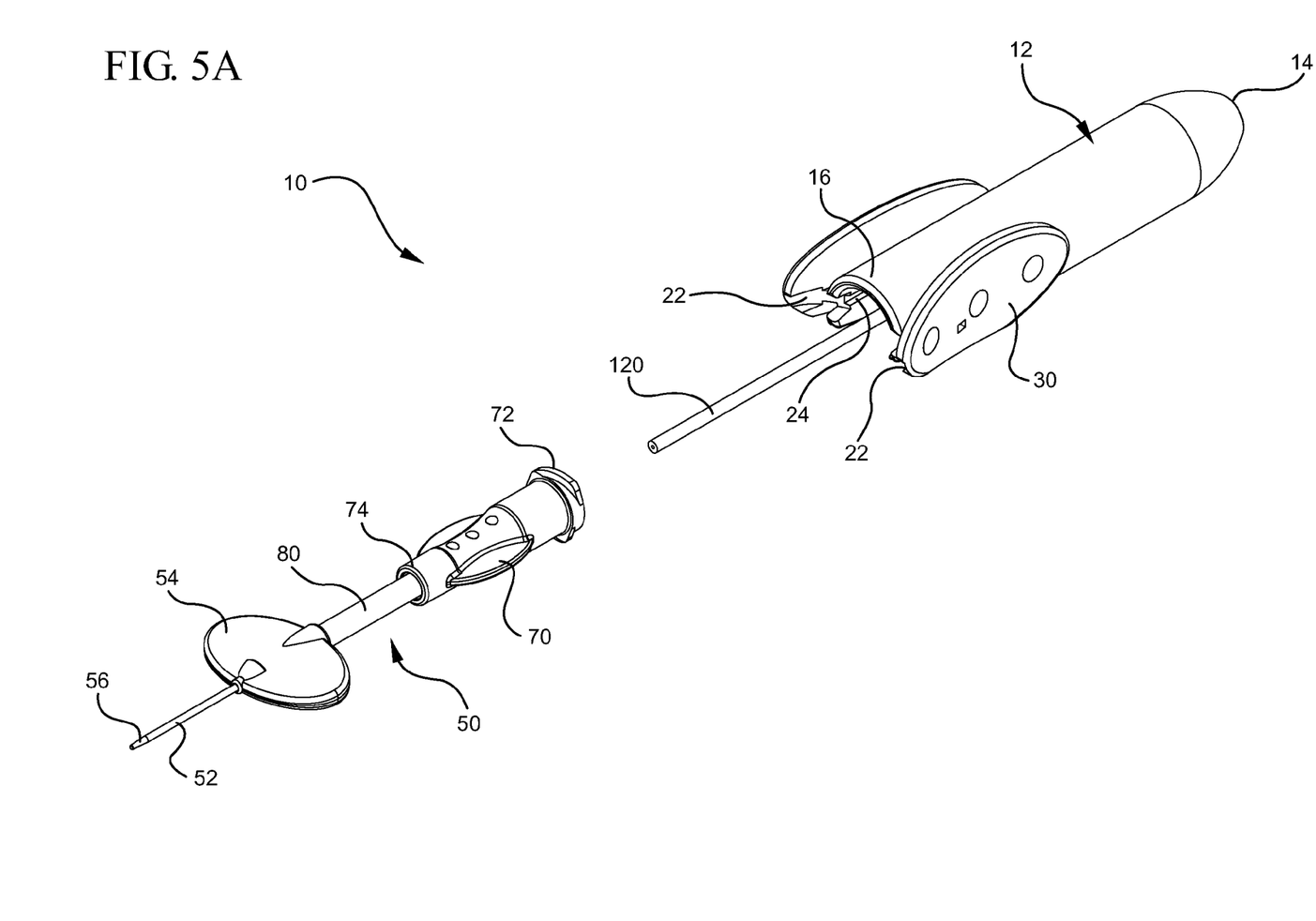
Figure 5B:
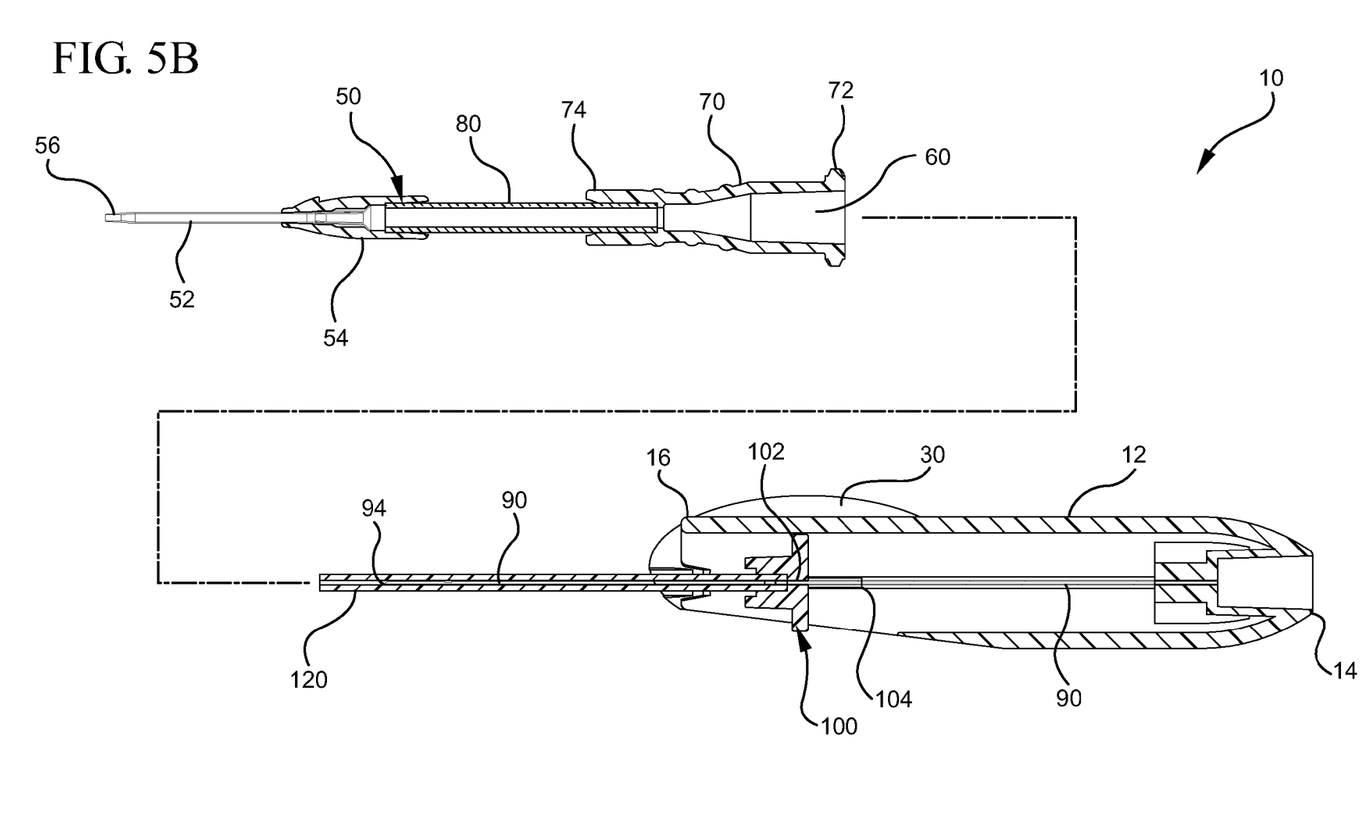

With continued reference to FIGS. 5A and 5B, catheter assembly 50 comprises an integral unit having common a fluid pathway 60 which is utilized to deliver an infusate to a patient. Following catheterization, needle adapter 12 and the various other components attached thereto are disposed.

Catheter adapter 54 is then secured to the patient via an adhesive strip or an elastic band.

Figure 6:
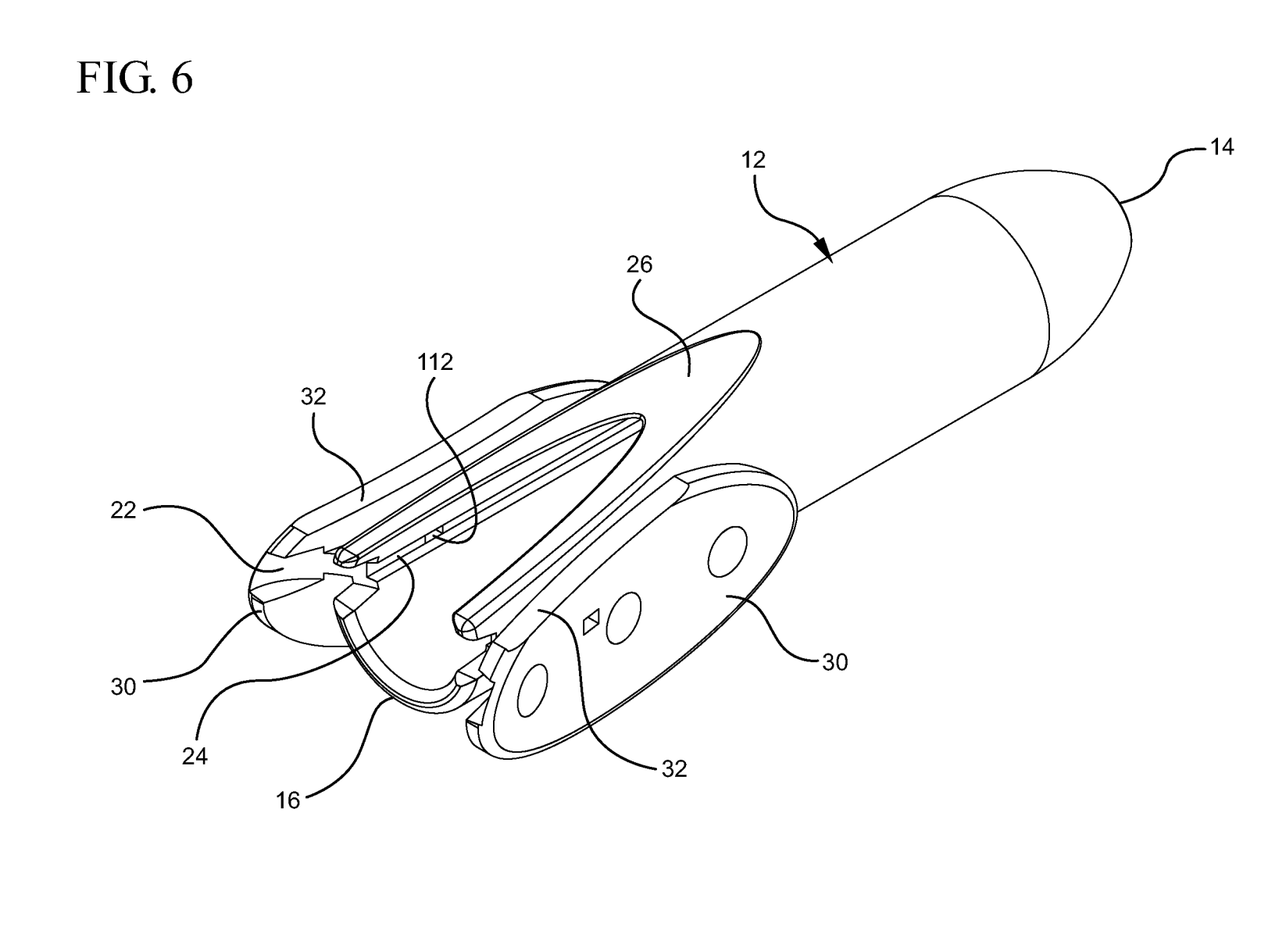
FIG. 6 is a detailed view of a needle adapter in accordance with a representative embodiment of the present invention.
Figure 7:
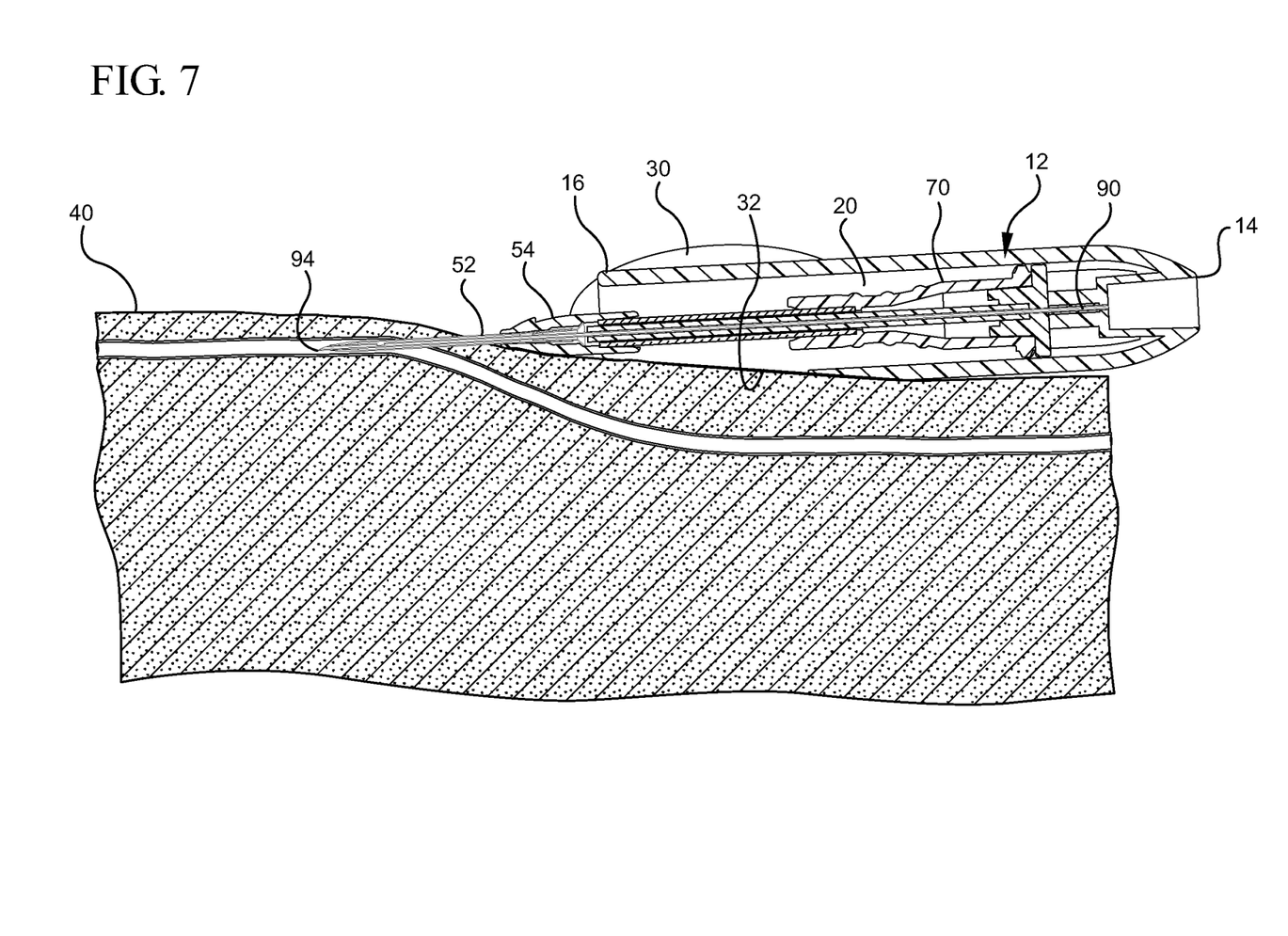
FIG. 7 is a cross-section view of an intravenous device following insertion and prior to removal of the needle adapter during an infusion procedure in accordance with a representative embodiment of the present invention.

Referring now to FIG. 6, a bottom perspective view of needle adapter 12 is shown. In some embodiments, an underside surface of needle adapter 12 comprises a cutaway 26 whereby the overall diameter of needle adapter 12 tapers inwardly towards distal end 16. Cutaway 26 enables closer proximity between catheter adapter 54 and the patient 40 during catheterization. This feature minimizes the transition angle of catheter tube 52 thereby reducing the probability of occluding catheter tube 52 during catheterization, as shown in FIG. 7. In some embodiments, gripping surface 30 further comprises truncated bottom surfaces 32 which provide a common plane across cutaway 26 and the underside surfaces of gripping surfaces 30, as shown in FIGS. 6 and 7.

With reference to FIGS. 8A and 8B, a catheter assembly 50 of the present invention is shown following catheterization of a patient 40. In some embodiments, catheter adapter 54 is made such that catheter tube 52 is angled towards the skin of patient 40 when catheter adapter 54 is lying flat against the patient's skin. As such, kinking or occlusion of catheter tube 52 is minimized and/or prevented. Catheter adapter 54 is further sized to allow easy taping 64 of the adapter to the small limbs of a premature baby.

In some embodiments, the length of extension tube 80 is selected to provide separation between the immobilized catheter adapter 54 and the luer adapter 70. As such, luer adapter 70 may be accessed and manipulated without disturbing the secured position of catheter adapter 54. This feature prevents kinking of catheter tube 52. Isolating catheter adapter 54 from luer adapter 70 further minimizes and/or prevents undesirable damage to the patient's vein 42 due to excessive movement of catheter tube 52 within vein 42. This feature further allows the physician or clinician to manipulate the luer adapter 70 without dislodging the catheter tube 52 or even bothering the injection site. Thus, extension tube 80 provides stress relief within the inserted catheter assembly 50.

The flexible nature of extension tube 80 allows a clinician to attach an extension set 130, or other intravenous device to luer adapter 70 and maintain the immobilized position of catheter adapter 54 and catheter tube 52. In some embodiments, the length of extension tube 80 is further selected to isolate movement of luer adapter 70 from catheter adapter 54 without adding excessive priming volume to the system. As the venous pressure of some neonatal patients is very low, in some embodiments the length of extension tube 80 is selected to allow blood flow through catheter assembly 50 without collapsing the patient's vein 42, yet still provide unrestrained movement of luer adapter 70.

The present invention may be embodied in other specific forms without departing from its structures, methods, or other essential characteristics as broadly described herein and claimed hereinafter. For example, the various features discussed herein may be incorporated into any intravascular device, including devices not intended for use in neonatal patients. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An intravenous device, comprising:
   a needle adapter having a proximal end, a distal end, an outer surface and an inner compartment, the distal end forming an opening into the inner compartment, a surface of the inner compartment including one or more channels that extend longitudinally along the surface, each channel including a recess positioned towards a distal end of the channel;
   a catheter assembly including a catheter tube coupled to a catheter adapter, the catheter assembly further including a luer adapter coupled to the catheter adapter via an extension tube, the extension tube being flexible, and a fluid pathway extending through the catheter tube, the catheter adapter, the extension tube and the luer adapter;
   an introducer needle having a proximal end, a distal end and a body extending therebetween, the proximal end being coupled to the proximal end of the needle adapter; and
   a safety clip contained within the inner compartment, the safety clip having an aperture through which the introducer needle is inserted, the safety clip further including one or more arms, each arm having a first surface that extends inwardly towards the safety clip and a second surface that extends outwardly away from the arm, the safety clip further including a needle sheath that extends distally from the aperture;
   wherein, prior to using the peripheral intravenous catheter, the safety clip is in a proximal position in which:
      the second surface of each arm is positioned within a corresponding one of the one or more channels and inwardly biased,
      the luer adapter is positioned within the first surface of each arm, the inward biasing of the second surface causing the first surface to lock the luer adapter within the inner compartment, and
      the introducer needle extends distally out through the catheter tube; and
   wherein, after inserting the catheter tube into a vasculature, the safety clip is configured to slide into a distal position in which:
      the second surface of each arm is aligned with the recess in the corresponding channel thereby allowing the corresponding arm to extend outwardly to unlock the corresponding first surface from the luer adapter and therefore allow the luer adapter to be removed from within the inner compartment; and
      the distal end of the introducer needle is contained within the needle sheath.

2. The intravenous device of claim 1, wherein, when the safety clip is in the distal position, the second surface of each arm is locked within the recess of the corresponding channel thereby preventing the distal end of the introducer needle from being removed from within the needle sheath.

3. The intravenous device of claim 1, wherein the one or more arms comprise two arms positioned on opposite sides of the safety clip.

4. The intravenous device of claim 1, wherein, when the safety clip is in the proximal position, the extension tube and the luer adapter are selectively housed entirely within the inner compartment.

5. The intravenous device of claim 1, wherein the inner compartment further comprises a-grooves into which a portion of the catheter adapter is seated when the safety clip is in the proximal position.

6. The intravenous device of claim 1, wherein, when the safety clip is in the proximal position, the needle sheath extends through the luer adapter and the extension tube and into the catheter adapter.

7. The intravenous device of claim 6, wherein the needle sheath is formed of a rigid material that creates a stiffening interface between the luer adapter and the catheter adapter.

8. The intravenous device of claim 1, wherein the catheter adapter has a disk shape.

9. An intravenous device system, comprising:

a needle adapter having a proximal end, a distal opening, an outer surface and an inner compartment, a surface of the inner compartment including a pair of channels that extend longitudinally along the surface, each channel including a recess positioned towards a distal end of the channel;

a catheter assembly partially housed within the inner compartment of the needle adapter, the catheter assembly comprising a catheter tube coupled to a catheter adapter, the catheter adapter further coupled to a luer adapter via a flexible extension tube, the catheter tube, the catheter adapter, the flexible extension tube and the luer adapter having a common fluid pathway;

an introducer needle having a proximal end, a distal tip and a body extending therebetween, the proximal end of the introducer needle being fixedly coupled to a proximal surface of the inner compartment, the body of the introducer needle extending distally through the common fluid pathway of the catheter assembly, wherein the distal tip of the introducer needle extends beyond a tip portion of the catheter tube;

a safety clip interposedly positioned between a proximal end of the luer adapter and the proximal end of the needle adapter, the safety clip having an aperture through which the introducer needle is inserted, the safety clip further including a pair of arms, each arm having a first surface interlockedly coupled to the luer adapter, and a second surface positioned within and outwardly biased against one of the channels, wherein contact between the second surface of each arm and the corresponding channel maintains the interlocked coupling of the corresponding first surface and the luer adapter, the safety clip further including a needle sheath that extends distally from the aperture;

wherein the safety clip is configured to slide distally within the inner compartment thereby causing the second surface of each arm to be aligned with the recess in the corresponding channel, and wherein, each recess is configured to allow the corresponding second surface to extend outwardly into the recess thereby unlocking the corresponding first surface from the luer adapter; and wherein, when the second surface of each arm is positioned within the corresponding recess, the distal tip of the introducer needle is contained within the needle sheath.

10. The intravenous device system of claim 9, wherein, when the arms are interlockedly coupled to the luer adapter, the needle sheath extends through the luer adapter and flexible tube and into the catheter adapter.

11. The intravenous device system of claim 10, wherein the needle sheath is formed of a rigid material that forms a stiffening interface between the catheter adapter and the luer adapter.

12. The intravenous device system of claim 9, wherein the catheter adapter is secured within grooves formed on an inside surface of the needle adapter.

13. The intravenous device system of claim 9, wherein the catheter adapter is disk shaped.

14. The intravenous device system of claim 9, wherein the needle adapter includes gripping surfaces positioned at a distal end and on opposite sides of the needle adapter, the gripping surfaces each including a groove within which the catheter adapter inserts.

* * * * *